(12) United States Patent
Kanemasa et al.

(10) Patent No.: US 10,537,706 B2
(45) Date of Patent: Jan. 21, 2020

(54) METHOD FOR MANUFACTURING MEDICAL INSTRUMENT, AND MEDICAL INSTRUMENT

(71) Applicant: SUMITOMO BAKELITE CO., LTD., Shinagawa-ku (JP)

(72) Inventors: Kenichi Kanemasa, Akita (JP); Hayao Tanaka, Akita (JP); Kenjiro Yamaguchi, Akita (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 543 days.

(21) Appl. No.: 14/377,389

(22) PCT Filed: Feb. 27, 2013

(86) PCT No.: PCT/JP2013/001151
§ 371 (c)(1),
(2) Date: Aug. 7, 2014

(87) PCT Pub. No.: WO2013/128910
PCT Pub. Date: Sep. 6, 2013

(65) Prior Publication Data
US 2015/0283356 A1    Oct. 8, 2015

(30) Foreign Application Priority Data

Feb. 28, 2012    (JP) .................................. 2012-041960

(51) Int. Cl.
*A61M 25/00* (2006.01)
*A61M 25/01* (2006.01)

(52) U.S. Cl.
CPC ..... *A61M 25/0012* (2013.01); *A61M 25/0023* (2013.01); *A61M 25/0032* (2013.01);
(Continued)

(58) Field of Classification Search
CPC ........ A61M 25/0147; A61M 2025/015; A61M 25/0133; A61M 25/0105; A61M 25/0032; A61M 25/0043; A61M 25/0023
See application file for complete search history.

(56) References Cited

U.S. PATENT DOCUMENTS

| | | | | | |
|---|---|---|---|---|---|
| 5,397,304 | A | * | 3/1995 | Truckai ............. | A61M 25/0147 604/528 |
| 5,593,394 | A | * | 1/1997 | Kanesaka ......... | A61M 25/0023 604/524 |

(Continued)

FOREIGN PATENT DOCUMENTS

| JP | 6-142207 | | 5/1994 |
|---|---|---|---|
| JP | 06142207 | A * | 5/1994 |

(Continued)

OTHER PUBLICATIONS

International Search Report dated May 28, 2013, in PCT/JP13/001151 filed Feb. 27, 2013.

*Primary Examiner* — Nilay J Shah
(74) *Attorney, Agent, or Firm* — Oblon, McClelland, Maier & Neustadt, L.L.P.

(57) ABSTRACT

A method for manufacturing a catheter includes a process of supplying a resin material in a melted state to the periphery of a core wire (90) and molding a hollow tube (82) having the core wire (90) inserted thereinto; a process of arranging the hollow tube (82) having the core wire (90) inserted thereinto, on an outer peripheral side of a main lumen forming region of a tubular body part (10) made of resin; a process of extracting the core wire (90) from the inside of the hollow tube (82) to form a sublumen after the core wire (90) inside the hollow tube (82) is elongated and reduced in diameter to peel off the hollow tube (82) and the core wire (90), and a process of inserting an operating wire into the hollow tube (82).

20 Claims, 11 Drawing Sheets

(52) U.S. Cl.
CPC ..... *A61M 25/0105* (2013.01); *A61M 25/0147* (2013.01); *F04C 2270/0421* (2013.01); *Y10T 29/49799* (2015.01)

(56) References Cited

U.S. PATENT DOCUMENTS

| | | | | |
|---|---|---|---|---|
| 5,810,869 | A * | 9/1998 | Kaplan | A61M 25/0014 604/96.01 |
| 5,897,529 | A * | 4/1999 | Ponzi | A61M 25/0147 604/524 |
| 7,591,813 | B2 | 9/2009 | Levine et al. | |
| 8,267,908 | B2 | 9/2012 | Coulthard | |
| 8,273,073 | B2 | 9/2012 | Levine et al. | |
| 2002/0082584 | A1 * | 6/2002 | Rosenman | A61M 25/0014 604/523 |
| 2002/0161353 | A1 * | 10/2002 | Kortelling | A61M 25/0144 604/528 |
| 2008/0167628 | A1 * | 7/2008 | Li | A61F 2/95 604/264 |
| 2012/0197240 | A1 * | 8/2012 | Smith | A61B 1/0055 606/1 |
| 2013/0197564 | A1 | 8/2013 | Levine et al. | |

FOREIGN PATENT DOCUMENTS

| | | |
|---|---|---|
| JP | 2004-222810 | 8/2004 |
| JP | 2007-507305 | 3/2007 |
| JP | 2011-250903 | 12/2011 |
| JP | 2011-251068 | 12/2011 |
| WO | WO 2010/059712 A2 | 5/2010 |

* cited by examiner

METHOD FOR MANUFACTURING MEDICAL INSTRUMENT, AND MEDICAL INSTRUMENT

TECHNICAL FIELD

The present invention relates to a method for manufacturing a medical instrument, and a medical instrument.

BACKGROUND ART

In recent years, catheters capable of bending at the distal end portion to operate the direction of entry into a body cavity have been provided. For example, a catheter in which a wire lumen (sublumen) is provided around a main lumen, and a push/pull wire is inserted through the sublumen is described in Patent Document 1. In this catheter, a tip of the catheter is bent by operating the push/pull wire.

RELATED DOCUMENT

Patent Document

[Patent Document 1] PCT Japanese Translation Patent Publication No. 2007-507305

DISCLOSURE OF THE INVENTION

In the catheter disclosed in Patent Document 1, it turns out that, when the catheter is manufactured, the shape of the sublumen is deformed and it is difficult to form the sublumen in a desired shape.

According to the invention, there is provided a method for manufacturing a medical instrument including a process of supplying a resin material to the periphery of a core wire and molding a hollow tube having the core wire inserted thereinto; a process of arranging the hollow tube having the core wire inserted thereinto, on an outer peripheral side of a main lumen forming region of a tubular body part made of resin; a process of extracting the core wire from the inside of the hollow tube to form a sublumen after the core wire inside the hollow tube is elongated and reduced in diameter to peel off the hollow tube and the core wire; and a process of inserting an operating wire into the hollow tube.

According to the invention, the hollow tube having the core wire inserted thereinto is formed by supplying the resin material to the periphery of the core wire. Therefore, the core wire and the inside of the hollow tube are brought into close contact with each other. Thereafter, the hollow tube in a state where the core wire is inserted thereinto is arranged on the outer peripheral side of the main lumen forming region of the tubular body part made of resin. Since the core wire is inserted into the hollow tube in a close contact state, the shape of the hollow tube is prevented from being deformed in a catheter manufacturing process.

Additionally, since the core wire may be elongated and reduced in diameter so as to peel off the hollow tube and the core wire when the core wire is removed from the hollow tube, the core wire can be easily removed from the hollow tube.

Additionally, according to the invention, the medical instrument manufactured by the above-described manufacturing method can be provided.

Meanwhile, the invention can provide a medical instrument including a tubular body part having a main lumen formed therein; and a hollow tube arranged on an outer peripheral side of the main lumen to demarcate a sublumen. An operating wire is loosely inserted to the hollow tube. An inner surface of the hollow tube is formed with a plurality of protrusions or a plurality of recesses that extend in a longitudinal direction of the hollow tube. The plurality of protrusions or the plurality of recesses are arranged apart from each other along the longitudinal direction of the hollow tube. A distal end portion of the tubular body part is bent by operating a proximal end of the operating wire.

Such a medical instrument can be manufactured by the above-described manufacturing method.

The inner surface of the hollow tube is formed with a plurality of protrusions or a plurality of recesses that extend in a longitudinal direction of the hollow tube. Since the plurality of protrusions or the plurality of recesses are arranged apart from each other along the longitudinal direction of the hollow tube, it is possible to reduce the area of contact between the inner surface of the hollow tube and the operating wire.

Accordingly, a medical instrument with excellent operativity can be provided.

According to the invention, the method for manufacturing a medical instrument and the medical instrument that can forma sublumen with a desired shape are provided.

BRIEF DESCRIPTION OF THE DRAWINGS

The above-described objects and other objects, features, and advantages will be apparent by the preferred embodiments to be described below, and the following drawings attached thereto.

FIG. 6 shows side views of the entire catheter, and shows an example of bending of a tip portion, of which FIG. 6(a) is a side view showing the entire catheter before being bent, FIG. 6(b) is a side view showing a state where a slider is operated to bend the tip upward, FIG. 6(c) is a side view showing a state where the slider is operated to bend the tip upward with a larger curvature than that of FIG. 6 (b), FIG. 6 (d) is a side view showing a state where the slider is operated to bend the tip downward, and FIG. 6(e) is a side view showing a state where the slider is operated to bend the tip downward with a larger curvature than that of FIG. 6(d).

DESCRIPTION OF EMBODIMENTS

Figure 1:
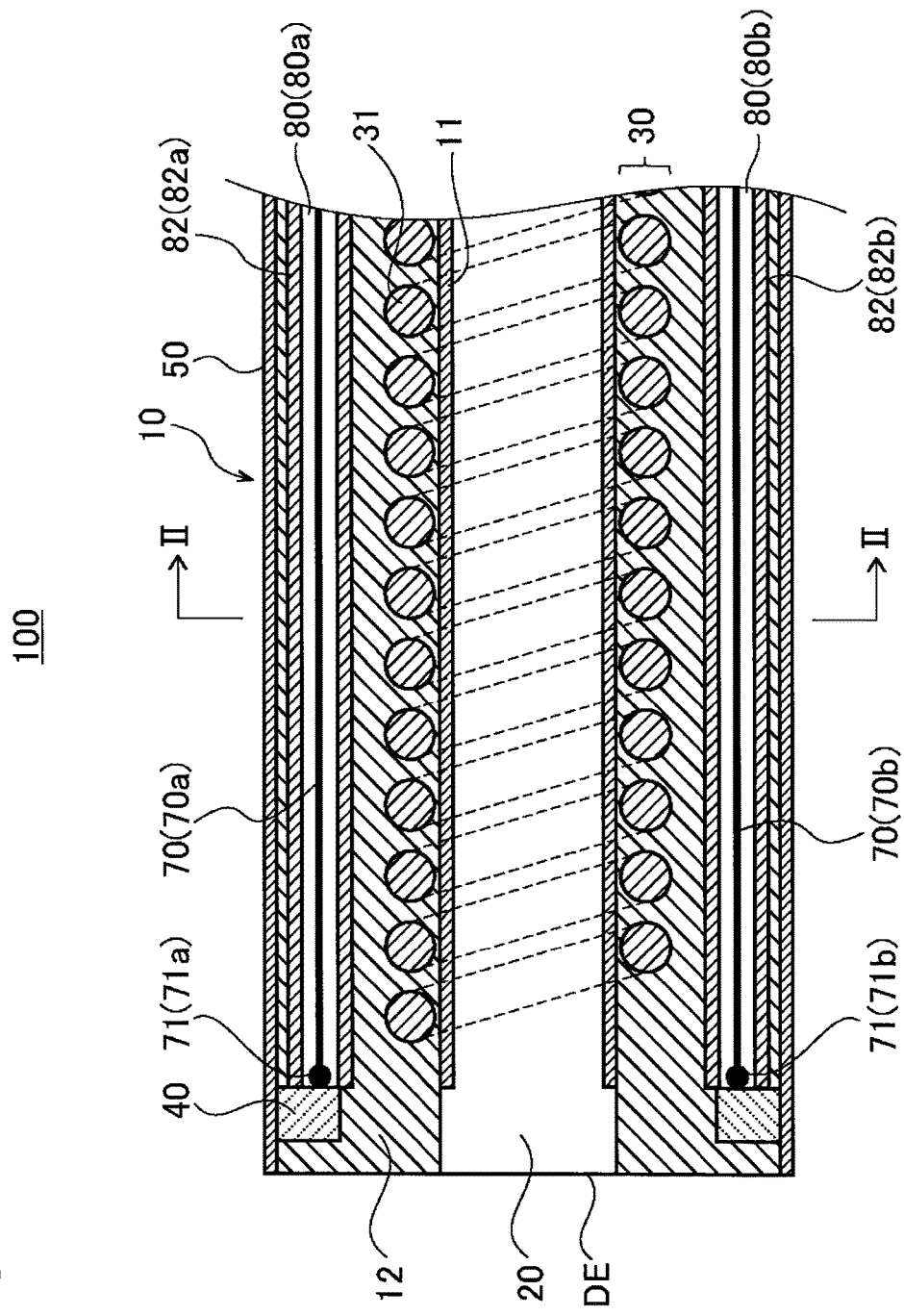
FIG. 1 is an enlarged view of a cross-section of a catheter related to an embodiment of the invention.

Hereinafter, an embodiment of the invention will be described with reference to the drawings. In addition, in all the drawings, the same constituent elements will be designated by the same reference numerals, and the detailed description thereof will not be appropriately repeated so as not to duplicate.

[Configuration Example]

Figure 2:
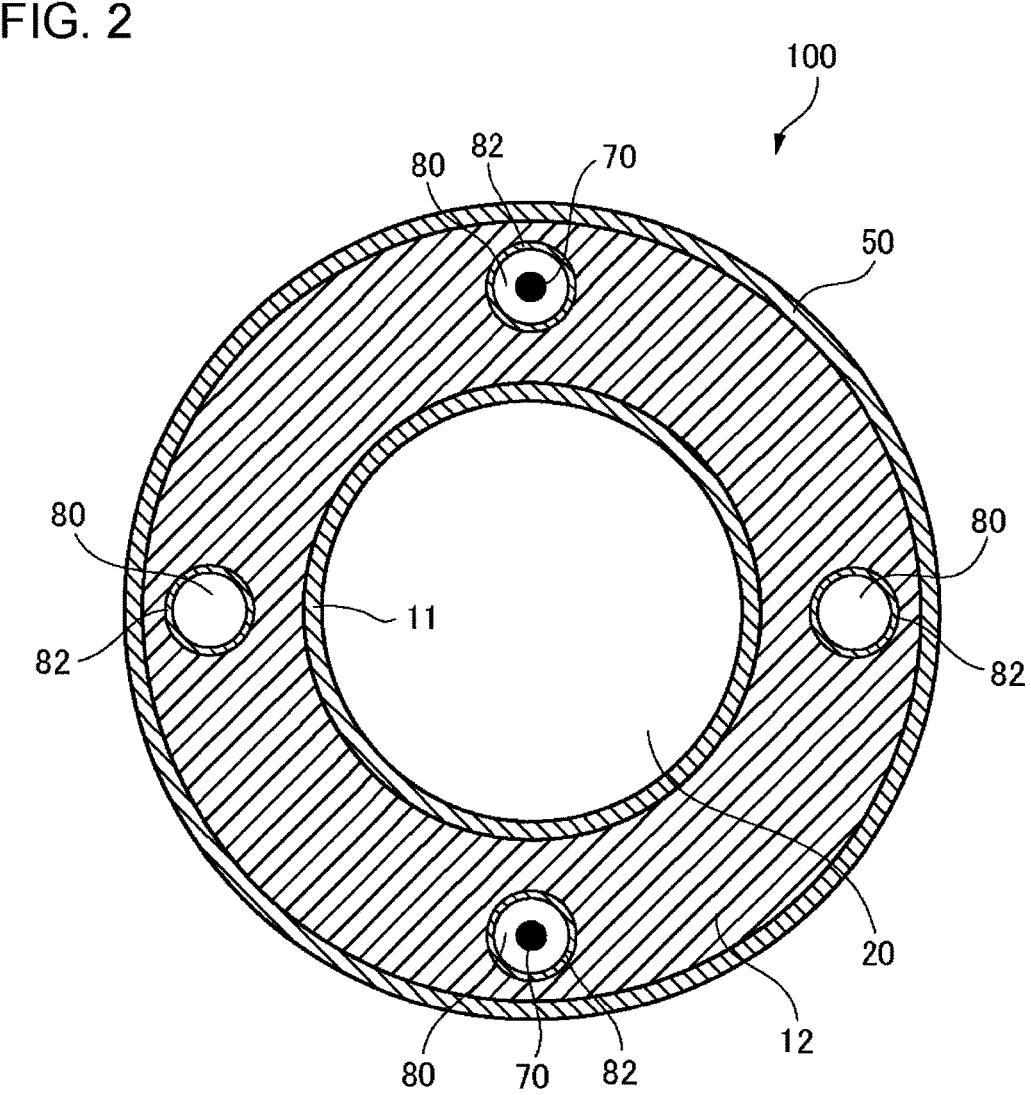
FIG. 2 is a cross-sectional view taken in direction II-II of FIG. 1.

The appearance of a catheter 100 that is a medical instrument of the present embodiment will be described with reference to FIGS. 1, 2, and 4. FIG. 1 is a cross-sectional view along a longitudinal direction of the catheter 100, and FIG. 2 is a cross-sectional view taken in direction II-II of FIG. 1. In addition, illustration of a reinforcing layer 30 is omitted in FIG. 2.

The catheter 100 of the present embodiment includes a tubular body part (sheath) 10 having a main lumen 20 formed therein, and hollow tubes 82 (82a, 82b) that are arranged on an outer peripheral side of the main lumen 20 and demarcate sublumens 80 (80a, 80b).

Operating wires 70 (70a, 70b) are loosely inserted to the hollow tubes 82 (82a, 82b). An inner surface of each hollow tube 82 is formed with a plurality of protrusions 822 or a plurality of recesses 821 that extend in a longitudinal direction of the hollow tube 82 and are spaced apart from each other (refer to FIG. 4). By operating proximal ends of the operating wires 70 (70a, 70b), a distal end portion of the sheath 10 is bent.

Next, the structure of the catheter 100 will be described in detail.

The catheter 100 includes a coating layer 50 and an operating part 60 (refer to FIG. 6), in addition to a tubular body having the tubular body part 10, and the operating wires 70.

The tubular body includes a sheath (tubular body part) 10 including an inner layer 11 having the main lumen therein and an outer layer 12 covering the inner layer 11, the reinforcing layer 30, the hollow tubes 82, and a marker 40.

In addition, hereinafter, although the tips of the sheath 10 and the catheter 100 are referred to as distal ends DE, a rear end of the sheath 10 is referred to as a proximal end PE, and a rear end of the catheter 100 is referred to as a proximal end CE.

The inner layer 11 is a hollow tubular layer, and the main lumen 20 extending along the longitudinal direction of the catheter 100 is formed in the inner layer. A fluorine-based thermoplastic polymer material, as an example, can be used for the inner layer 11. More specifically, any one or more of polytetrafluoroethylene (PTFE), polyvinylidene fluoride (PVDF), and perfluoroalkoxy fluororesin (PFA) can be used. By using fluorine-based resin for the inner layer 11, the delivery performance when a contrast medium, a medical fluid, or the like is supplied to an affected part through the main lumen 20 of the catheter 100 is excellent.

The cross-sectional shape of the main lumen 20 orthogonal to the longitudinal direction of the catheter 100 is a circular shape.

The outer layer 12 is a tubular member made of resin that covers the inner layer 11. The outer layer 12 is thicker than the inner layer 11, and constitutes the main thickness of the sheath 10.

A thermoplastic polymer is widely used for the outer layer 12. Any one or more of polyethylene (PE), polyamide (PA), nylon elastomer, polyurethane (PU), ethylene-vinyl acetate resin (EVA), polyvinyl chloride (PVC), or polypropylene (PP), and the like in addition to polyimide (PI), polyamide imide (PAI), and polyethylene terephthalate (PET) can be used as an example.

The reinforcing layer 30 surrounds the inner layer 11, and is encapsulated in the outer layer 12. The reinforcing layer 30 is a coil 31. Thin wires of polymer fibers, such as PI, PAI, or PET in addition to thin metallic wires, such as stainless steel (SUS) and a nickel titanium alloy, can be used for a wire material that constitutes the reinforcing layer 30. Additionally, the cross-sectional shape of the wire material is not particularly limited, and a round wire and a flat wire may be used.

In addition, in the catheter 100 of the present embodiment, the sublumens 80 through which the operating wires 70 are inserted, respectively are formed inside the outer layer 12 and outside the reinforcing layer 30.

The operating wire 70 is loosely inserted to the sublumen 80, and extends along a longitudinal direction of the sublumen 80.

Figure 3:
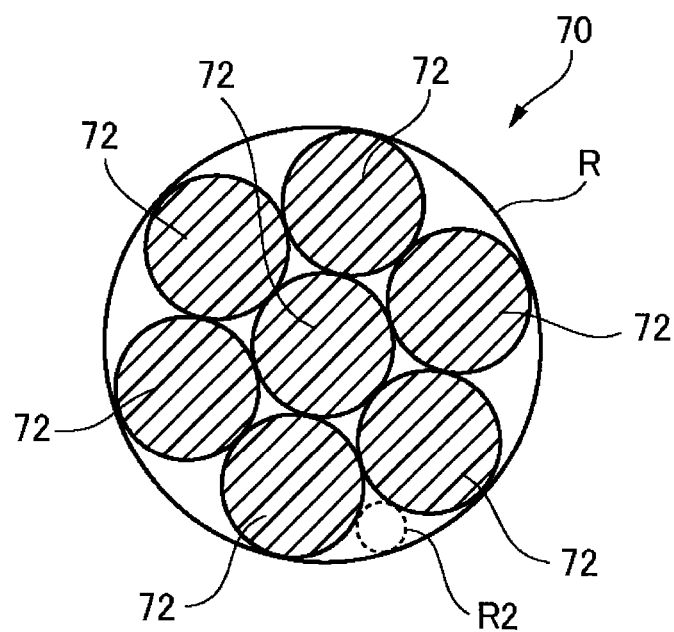
FIGS. 3(a) and 3(b) are cross-sectional views of an operating wire.
Figure 3:
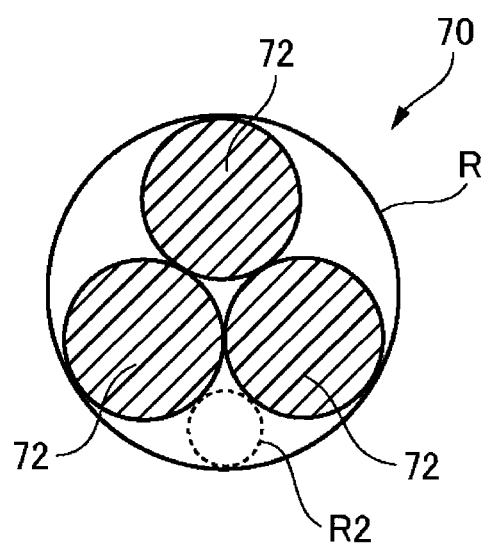

Although the operating wire 70 may be constituted by one wire, as shown in FIG. 3, a stranded wire configured by twisting a plurality of thin wires 72 together is preferable. When the operating wire 70 is constituted by one wire, a cross-section orthogonal to a longitudinal direction is a circular shape. Similarly, when the operating wire 70 is constituted by a stranded wire, the cross-section of the thin wires 72 constituting the operating wire 70, which is orthogonal to the longitudinal direction, is a circular shape.

Here, the cross-section being the circular shape is not limited to a true circle.

When the operating wire 70 is constituted by the stranded wire, it is preferable that the operating wire have a structure in which the thin wires 72 are arranged so that the respective thin wires 72 constituting the outline of the operating wire 70 are inscribed on one circle R in the cross-section orthogonal to the longitudinal direction.

Here, although the number of the thin wires constituting one stranded wire is not limited, it is preferable to provide three or more thin wires. A suitable example of the number of the thin wires is 3 or 7. When the number of the thin wires is three, the three thin wires are point-symmetrically arranged in a cross-section. When the number of the thin wires is seven, the seven thin wires are point-symmetrically arranged in the shape of a honeycomb in a cross-section.

As shown in FIG. 1, the hollow tubes 82 (82a, 82b) are embedded within the outer layer 12, and are arranged around the main lumen 20 so that the longitudinal direction thereof runs along the longitudinal direction of the main lumen 20. The hollow tube 82 demarcates the sublumen 80.

The hollow tube 82 that demarcates the sublumen 80 is provided along the longitudinal direction of the catheter 100, and although not shown, the hollow tube opens at the proximal end PE side of the sheath 10. Additionally, the portion of the hollow tube 82 on the distal end side of the sheath 10 is closed by the marker 40.

The hollow tubes 82 are arranged outside the reinforcing layer 30, and the inside of the reinforcing layer 30, that is, the main lumen 20, is protected from the operating wires 70 (70a, 70b) arranged inside the hollow tubes 82.

In the present embodiment, as shown in FIG. 2, the plurality of hollow tubes 82 are provided. Specifically, the plurality of hollow tubes 82 are arranged on the same circumference so as to surround the main lumen 20. In the present embodiment, four hollow tubes 82 are arranged at equal intervals. The operating wires 70 are arranged inside a pair of hollow tubes 82 that face each other with the center of the main lumen 20 therebetween. Additionally, the operating wires 70 are not arranged inside another pair of hollow tubes 82 that face each other with the center of the main lumen 20 therebetween.

In addition, the number of the hollow tubes 82 or the sublumens 80 is not limited to four, and can be appropriately selected if necessary.

Figure 4:
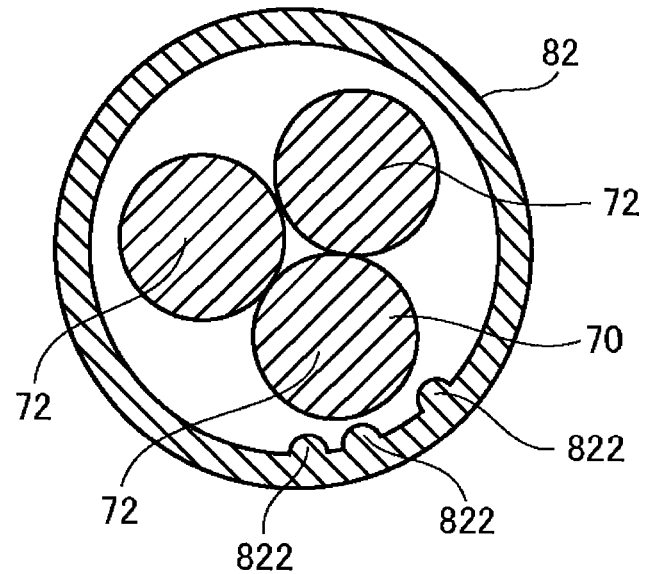
FIGS. 4(a) and 4(b) are cross-sectional views orthogonal to a longitudinal direction of a hollow tube, showing the operating wire and the hollow tube.
Figure 4:
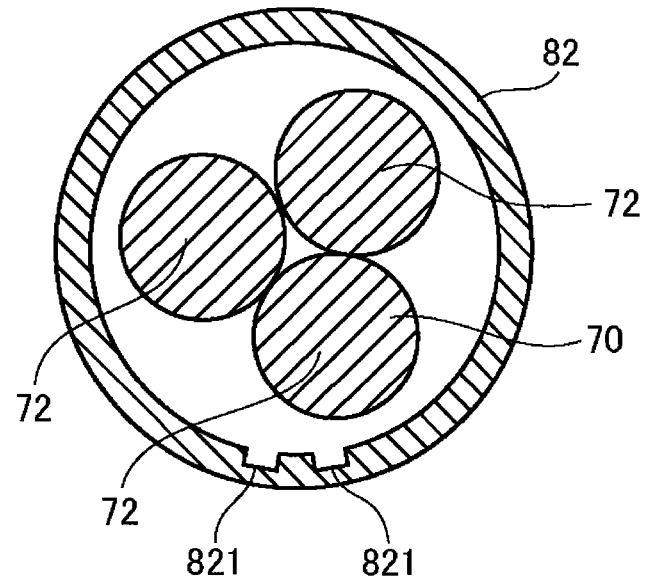
Figure 5:
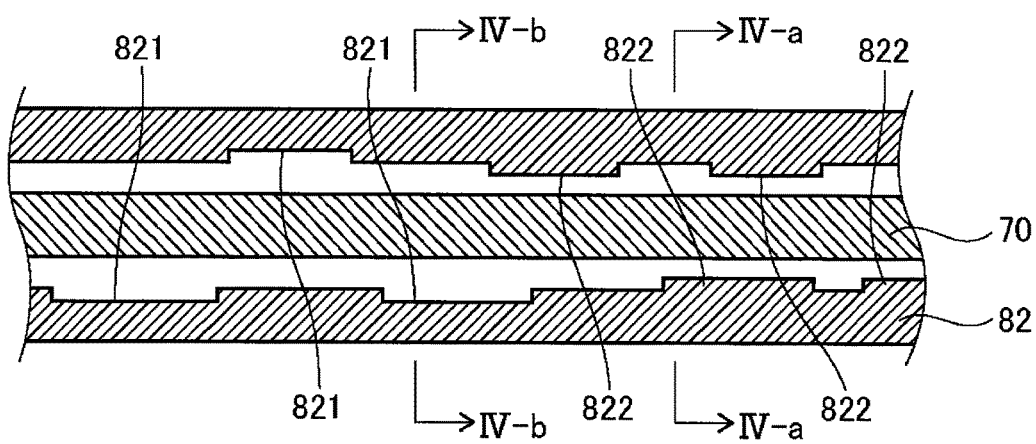
FIG. 5 is a cross-sectional view along the longitudinal direction of the hollow tube and the operating wire.

A cross-sectional view of the hollow tube 82 in a direction orthogonal to the longitudinal direction is shown in FIG. 4. Additionally, a cross-sectional view along the longitudinal direction of the hollow tube 82 is shown in FIG. 5. An IV-a-IV-a cross-section of FIG. 5 is FIG. 4(a), and an IV-b-IV-b cross-section is FIG. 4(b).

As shown in FIG. 4, the outer shape of the hollow tube 82 in a cross-section orthogonal to the longitudinal direction of the hollow tube is a circular shape. In the sublumen 80 inside the hollow tube 82, a cross-sectional shape orthogonal to the longitudinal direction of the catheter 100 is also a substantially circular shape.

As shown in FIGS. 4 and 5, an inner surface of the hollow tube 82 is formed with the plurality of recesses 821 and the plurality of protrusions 822. These recesses 821 and the protrusions 822 extend along the longitudinal direction of the hollow tube 82, respectively.

Here, one recess 821 is not formed over the total length of the hollow tube 82 in the longitudinal direction, but a plurality of recesses 821 are arranged apart from each other along the longitudinal direction of the hollow tube.

Additionally, it is preferable that the plurality of recesses 821 be different from each other in terms of at least any one of length (length along the longitudinal direction of the hollow tube 82), depth, width (length in a direction orthogonal to the depth and the length), and a cross-sectional shape. Accordingly, for example, even if the operating wire 70 gets stuck in the plurality of recesses 821, a difference occurs between the degrees of sticking. Thus, the operating wire 70 can be easily extracted from the recesses 821, and the operativity of the operating wire 70 is not hindered.

It should be noted that the recesses 821 having the same shape and size may be formed.

The cross-sectional shape of the recesses 821 orthogonal to the longitudinal direction of the hollow tube is not limited, for example, the cross-sectional shape can be a V-shaped groove or a U-shaped groove.

It is preferable that the width of each recess 821 be smaller than the diameter of the operating wire 70. Especially, as shown in FIG. 3, when the operating wire 70 is a stranded wire obtained by twisting a plurality of thin wires 72, it is preferable that the width of the recess 821 is smaller than the diameter of the thin wires 72.

This prevents the operating wire 70 from entering the recess 821.

Here, the depth of the recess 821 can be 0.5 µm to 3 µm, and the width of the recess can be 0.5 µm to 3 µm. Additionally, the depth and width of the recess 821 can be about 5% to 10% of the thickness of the hollow tube 82. Additionally, although the length of the recess 821 is not particularly limited, it is preferable that the length be greater than the width, and the length can be, for example, 1 µm to 100 µm.

Additionally, the plurality of protrusions 822 are arranged apart along the longitudinal direction of the hollow tube 82 on the inner surface of the hollow tube 82. One protrusion does not extend over the total length of the hollow tube 82 in the longitudinal direction. Moreover, although the recess 821 and the protrusion 822 are adjacent to each other along the longitudinal direction of the hollow tube 82, the recess 821 and the protrusion 822 are also spaced apart from each other.

In the cross-section orthogonal to the longitudinal direction of the hollow tube 82, the curvature radius of the protrusion 822 is smaller than the curvature radius of the operating wire 70. This can effectively reduce the area of contact between the operating wire 70 and the inner surface of the hollow tube 82.

Here, when the operating wire is constituted by one round wire, the curvature radius of the operating wire 70 is the curvature radius of the round wire in the cross-section orthogonal to the longitudinal direction of the operating wire. Meanwhile, when the operating wire 70 is constituted by the stranded wire, the curvature radius of the operating wire 70 is a curvature radius in a cross-section orthogonal to the longitudinal direction of the thin wire 72 that constitutes the operating wire 70.

Moreover, as shown in FIG. 3, when the operating wire 70 is the stranded wire configured by twisting the plurality of thin wires 72 together, it is preferable that the height of the protrusion 822 and the width of the protrusion 822 be smaller than the diameter of a inscribed circle R2 comes into contact with an circumscribed circle R of the stranded wire and two adjacent thin wires that constitute an outer peripheral portion of the stranded wire. This can prevent the protrusion 822 from being stuck between the thin wires 72 of the stranded wire.

Additionally, it is preferable that the plurality of protrusions 822 be different from each other in terms of at least any one of length (length along the longitudinal direction of the hollow tube 82), height, width (length in a direction orthogonal to the height and the length), and a cross-sectional shape. It should be noted that the protrusions 822 having the same shape and size may be formed.

Here, the height of the protrusion 822 can be 0.5 µm to 3 µm, and the width of the protrusion can be 0.5 µm to 3 µm. Additionally, the depth and width of the protrusion 822 can be about 5% to 10% of the thickness of the hollow tube 82. Additionally, although the length of the protrusion 822 is not particularly limited, it is preferable that the length be greater than the width, and the length can be, for example, 1 µm to 100 µm.

Additionally, an outer peripheral surface of the hollow tube 82 may be formed with fine irregularities, though not shown, and the outer peripheral surface may be roughened. When the fine irregularities are formed, it is preferable that the surface roughness (Ra) of the outer peripheral surface of the hollow tube 82 be 0.1 µm to 0.3 µm. It is preferable that the fine irregularities of the outer peripheral surface of the hollow tube 82 be embedded in the outer layer 12.

The hollow tube 82 is made of a material different from that of the outer layer 12. This enables the hollow tube 82 to be made of a material having bending rigidity and tensile elasticity higher than the outer layer 12. For example, the materials that constitute the hollow tube 82 include polytetrafluoroethylene (PTFE), perfluoroalkoxy fluororesin (PFA), and tetrafluoroethylene-hexafluoropropylene copolymer (FEP). It is preferable to use anyone or more of these materials as main components. These materials can improve the slidability of the operating wire, and also have high heat resistance.

By using such a hollow tube 82, the torsional rigidity of the catheter 100 can be enhanced, and when the sheath is rotated with its longitudinal direction as a rotational axis, the sheath can be prevented from being locally twisted.

Additionally, as shown in FIG. 1, as the tip portions 71 (71a, 71b) of the operating wires 70 (70a, 70b) are fixed to the marker 40 at the distal end DE of the sheath 10, the tip portions 71 (71a, 71b) of the operating wires 70 (70a, 70b) are fixed to the distal end DE. The operating wires 70 are slidably inserted through the sublumens 80 (80a, 80b), respectively. The distal end portion 15 of the catheter 100 is bent by pulling the proximal ends of the respective operating wires 70 (70a, 70b) (refer to FIG. 6). Additionally, in the catheter 100 of the present embodiment, a curvature and a direction of the distal end portion 15 to be bent changes in multiple ways depending on the selection of the operating wires 70 (70a, 70b) to be pulled.

Here, as a specific material of the operating wire 70, for example, a polymer fiber made of any one or more of polyetheretherketone (PEEK), polyphenylene sulfide (PPS), polybutylene terephthalate (PBT), PI, PTFE, and the like, or a metal wire made of any one or more of SUS, a steel wire coated with corrosion resistance, titanium, a titanium alloy, and the like can be used. Additionally, in addition to the above respective materials, PVDF, high-density polyethylene (HDPE), polyester, or the like can also be used.

Figure 6:
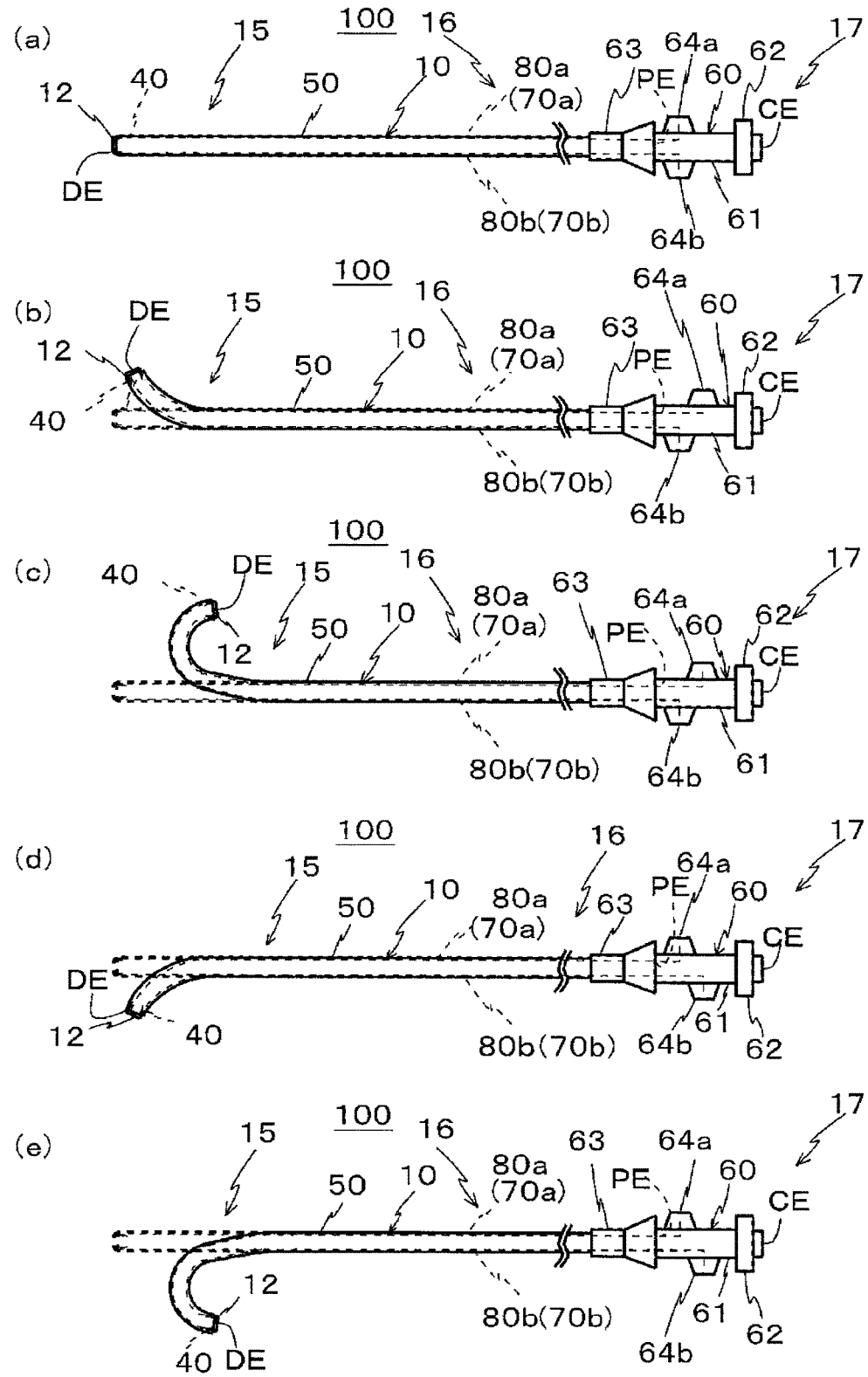

Additionally, as shown in FIG. 6, the catheter 100 includes the operating part 60. The operating part 60 is provided at a proximal end portion 17 of the catheter 100. Additionally, a portion between the distal end portion 15 and the proximal end portions 17 is referred to as an intermediate portion 16.

The operating part 60 includes a shaft portion 61 that extends in the longitudinal direction of the catheter 100, sliders 64 (64a, 64b) that advance and retract, respectively, in the longitudinal direction of the catheter 100 with respect to the shaft portion 61, and a handle portion 62 that rotates with the shaft portion 61 as an axis, and a gripping portion 63 through which the sheath 10 is rotatably inserted. Additionally, the proximal end portion 17 of the sheath 10 is fixed to the shaft portion 61. Additionally, the handle portion 62 and the shaft portion 61 are integrally configured. By rotating the gripping portion 63 and the handle portion 62 relative to each other, the whole sheath 10 including the operating wires 70 is torque-rotated together with the shaft portion 61.

Accordingly, the operating part 60 of the present embodiment rotationally operates the distal end portion 15 of the sheath 10. In addition, in the present embodiment, the handle portion 62 as a rotation operating portion that torque-rotates the sheath 10, and the sliders 64 as a bending operating part that bends the sheath 10 are integrally provided. However, the invention is not limited to this, and the handle portion 62 and the sliders 64 may be separately provided.

A proximal end of a first operating wire 70a is protruded from the proximal end portion 17 of the sheath 10 to a base end side, and is connected to a slider 64a of the operating part 60. Additionally, a proximal end of a second operating wire 70b is similarly connected to a slider 64b of the operating part 60. By causing the slider 64a and slider 64b to slide individually to the base end side with respect to the shaft portion 61, the first operating wire 70a or the second operating wire 70b connected to this slider is pulled, and a pulling force is applied to the distal end portion 15 of the sheath 10. Accordingly, the distal end portion 15 is bent to the pulled operating wire 70 side.

As shown in FIG. 1, the marker 40 is provided at the distal end of the sheath 10. The marker 40 is a ring-shaped member made of impermeant material through which radiation, such as X-rays, is not transmitted. Specifically, metallic materials, such as platinum, can be used for the marker 40. The marker 40 of the present embodiment is provided inside the outer layer 12 around the main lumen 20.

The coating layer 50 constitutes an outermost layer of the catheter 100, and is a hydrophilic layer. Hydrophilic materials, such as polyvinyl alcohol (PVA) and polyvinyl pyrrolidone, can be used for the coating layer 50.

Here, the typical dimensions of the catheter 100 of the present embodiment will be described. The radius of the main lumen 20 can be about 200 µm to 300 µm, the thickness of the inner layer 11 can be about 10 µm to 30 µm, the thickness of the outer layer 12 can be about 50 µm to 150 µm, the external diameter (diameter) of the reinforcing layer 30 can be about 500 µm to 860 µm, and the internal diameter (diameter) of the reinforcing layer 30 can be about 420 µm to 660 µm. The radius from an axial center of the catheter 100 to the center of the sublumen 80 can be about 300 µm to 350 µm, the internal diameter of the sublumen 80 can be about 40 µm to 100 µm, and the thickness of the operating wire 70 can be about 30 µm to 60 µm. Additionally, the wall thickness of the hollow tube can be about 3 µm to 15 µm. The outermost diameter (radius) of the catheter 100 can be about 350 µm to 490 µm.

That is, the external diameter of the catheter 100 of the present embodiment is less than 1 mm in diameter, and the catheter is insertable through blood vessels, such as the celiac artery. Additionally, regarding the catheter 100 of the present embodiment, a traveling direction of the catheter is freely operated by the pulling of the operating wires 70 (70a, 70b). Therefore, it is also possible to cause the catheter 100 to enter, for example, a branching blood vessel in a desired direction.

[Example of Operation]

Next, an example of operation of the catheter 100 of the present embodiment will be described with reference to FIG. 6. First, in the catheter 100 of the present embodiment, if the proximal end of the operating wire 70 (the first operating wire 70a or the second operating wire 70b) is pulled, a pulling force is applied to the distal end portion 15 of the catheter 100, and a portion or the entirety of the distal end portion 15 is bent toward the sublumen 80 (a sublumen 80a or a sublumen 80b) side through which the operating wire 70 (the first operating wire 70a or the second operating wire 70b) is inserted. Meanwhile, when the proximal end of the operating wire 70 is pushed into the catheter 100, a substantial pushing force is not applied to the distal end portion 15 of the catheter 100 from the operating wire 70.

In addition, the distal end portion 15 of the catheter 100 indicates a predetermined length region including the distal end DE of the catheter 100. Similarly, the proximal end portion 17 of the catheter 100 indicates a predetermined length region including the proximal end CE of the catheter 100. The intermediate portion 16 indicates a predetermined length region between the distal end portion 15 and the proximal end portion 17. Additionally, the catheter 100 being bent means that a portion or the entirety of the catheter 100 is curved or bent.

In the catheter 100 of the present embodiment, the curvature of the distal end portion 15 to be bent changes in multiple ways by using only the first operating wire 70a or only the second operating wire 70b as the operating wire 70 to be pulled or simultaneously pulling the two operating wires 70a and 70b. This enables the catheter 100 to freely enter a branching body cavity at various angles.

In the catheter 100 of the present embodiment, the proximal ends of the plurality of operating wires 70 (the first operating wire 70a or the second operating wire 70b) can be individually pulled, respectively. The bending direction can be changed depending on the operating wires 70 to be pulled. Specifically, if the first operating wire 70a is pulled as shown in FIGS. 6(b) and 6(c), bending happens toward a side where the first operating wire 70a is provided, and if the second operating wire 70b is pulled as shown in FIGS. 6(d) and 6(e), bending happens toward a side where the second operating wire 70*b* is provided. Additionally, the curvature (curvature radius) of bending can be changed by adjusting the amount of pulling of each operating wire 70 (70*a*, 70*b*). Specifically, as shown in FIGS. 6(*b*) and 6(*d*), when the first or the second operating wire 70*a* or 70*b* is slightly pulled, the distal end portion 15 is bent with a small curvature (a large curvature radius). Meanwhile, as shown in FIGS. 6(*c*) and 6(*e*), when the first or the second operating wire 70*a* or 70*b* is pulled to be longer, the distal end portion 15 is bent with a larger curvature (a small curvature radius).

[Manufacturing Method]

Next, a method for manufacturing the catheter 100 of the present embodiment will be described with reference to FIGS. 7 to 9.

First, the outline of the method for manufacturing the catheter 100 will be described.

A method for manufacturing the catheter 100 of the present embodiment includes a process of supplying a liquid resin material to the periphery of a core wire 90 and molding a hollow tube 82 having the core wire 90 inserted thereinto; a process of arranging the hollow tube 82 having the core wire 90 inserted thereinto, on an outer peripheral side of a main lumen forming region of a tubular body part 10 made of resin; a process of extracting the core wire 90 from the inside of the hollow tube 82 to form a sublumen 80 after the core wire 90 inside the hollow tube 82 is elongated and reduced in diameter to peel off the hollow tube 82 and the core wire 90, and a process of inserting an operating wire 70 into the hollow tube 82.

Next, the method for manufacturing the catheter 100 will be described in detail.

First, an outer layer 12 is extrusion-molded. A material including resin that constitutes the outer layer 12 is extruded to the periphery of a mandrel (core material) that is not shown. At this time, extrusion molding is performed while a fluid, such as gas, is discharged so that elongated hollow portions (holes) along a longitudinal direction are respectively formed in the outer layer 12 at positions where sublumens 80 are formed by hollow tubes 82 being embedded afterwards.

A hollow-shaped outer layer 12 can be made by pulling out the mandrel after the extrusion molding.

Meanwhile, the hollow tube 82 is molded. First, the core wire 90 is prepared as shown in FIG. 7(*a*). Next, as shown in FIG. 7(*b*), a material including resin that constitutes the hollow tube 82 is melted and extruded to the periphery of the core wire 90 (a liquid resin material is supplied to the periphery of the core wire 90). Accordingly, the periphery of the core wire 90 is covered with the resin material, and the hollow tube 82 of which the inner surface is brought into close contact with the core wire 90 is obtained.

In addition, although the material including resin that constitutes the hollow tube 82 is melted and extruded to the periphery of the core wire 90, the hollow tube 82 may be manufactured through dispersion molding without being limited to this. Specifically, a water solution (liquid resin material) including the resin material that constitutes the hollow tube 82 is prepared. Then, the core wire 90 is dipped in this water solution, and is passed through the water solution. Accordingly, a film made of the resin material is formed at the periphery of the core material 90. Thereafter, the film is dried and baked. The hollow tube 82 of which the inner surface is brought into close contact with the core wire 90 can also be obtained by such a method.

At this time, the cross-section of the core wire 90 orthogonal to the longitudinal direction of the core wire is circular, and the cross-sectional shape of the hollow tube orthogonal to the longitudinal direction is also a circular ring shape.

Figure 7:
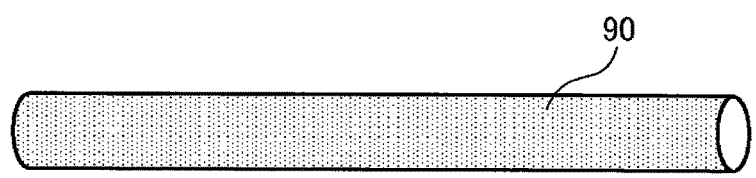
FIG. 7(a) is a perspective view showing a core wire.
FIG. 7(b) is a cross-sectional view along a longitudinal direction of a core wire and the hollow tube.
Figure 7:
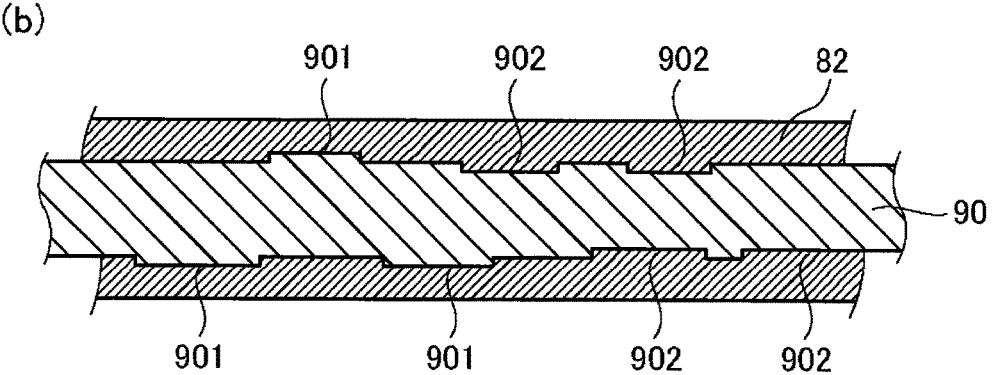

Additionally, an outer peripheral surface of the core wire 90, as shown in FIG. 7(*b*), is formed with a plurality of protrusions 901 and recesses 902 that extend along the longitudinal direction of the core wire. The protrusions 901 are arranged apart from each other along the longitudinal direction of the core wire 90. Similarly, the recesses 902 are arranged apart from each other along the longitudinal direction of the core wire 90.

The protrusions 901 and the recesses 902 correspond to the recesses 821 and the protrusion 822 of the aforementioned hollow tube 82, and the shapes of the protrusions 901 and the recesses 902 in the outer peripheral surface of the core wire 90 are transferred to the hollow tube 82 whereby the aforementioned recesses 821 and protrusions 822 are formed.

The materials of the core wire 90 include metallic materials, such as SUS. In addition, a method of forming the core wire 90 with the protrusions 901 and the recesses 902 includes, for example, a method of cutting the outer peripheral surface of the core wire 90 to form the protrusions 901 and the recesses 902. Additionally, when a wire material that serves as a raw material of the core wire 90 is drawn, the core wire 90 may be manufactured by using a die in which protrusions and recesses corresponding to the protrusions 901 and the recesses 902 are formed, and passing the wire material serving as the raw material of the core wire 90 through this die.

Next, the outer peripheral surface of the hollow tube 82 is surface-treated. For example, adhesion with the outer layer 12 is improved by performing plasma treatment or sodium treatment on the outer peripheral surface of the hollow tube 82 and performing reforming of the outer peripheral surface of the hollow tube 82.

Moreover, an inner layer 11 is also made by extrusion molding. Similarly to the case where the outer layer is formed, a material including resin that constitutes the inner layer 11 is extruded to the periphery of the mandrel (core material) M shown in FIG. 8.

Thereafter, a coil 31 is put on the periphery of the inner layer 11 with the core material M. Accordingly, the mandrel M is still inserted within the inner layer 11 at this stage.

In addition, the mandrel M can be made using the same material as the core wire 90.

Thereafter, the outer layer 12 covers the periphery of the coil 31 in a state where the coil 31 is put on the periphery of the inner layer 11.

Next, the hollow tube 82 with the core wire 90 is inserted into a hollow portion of the outer layer 12.

Figure 8:
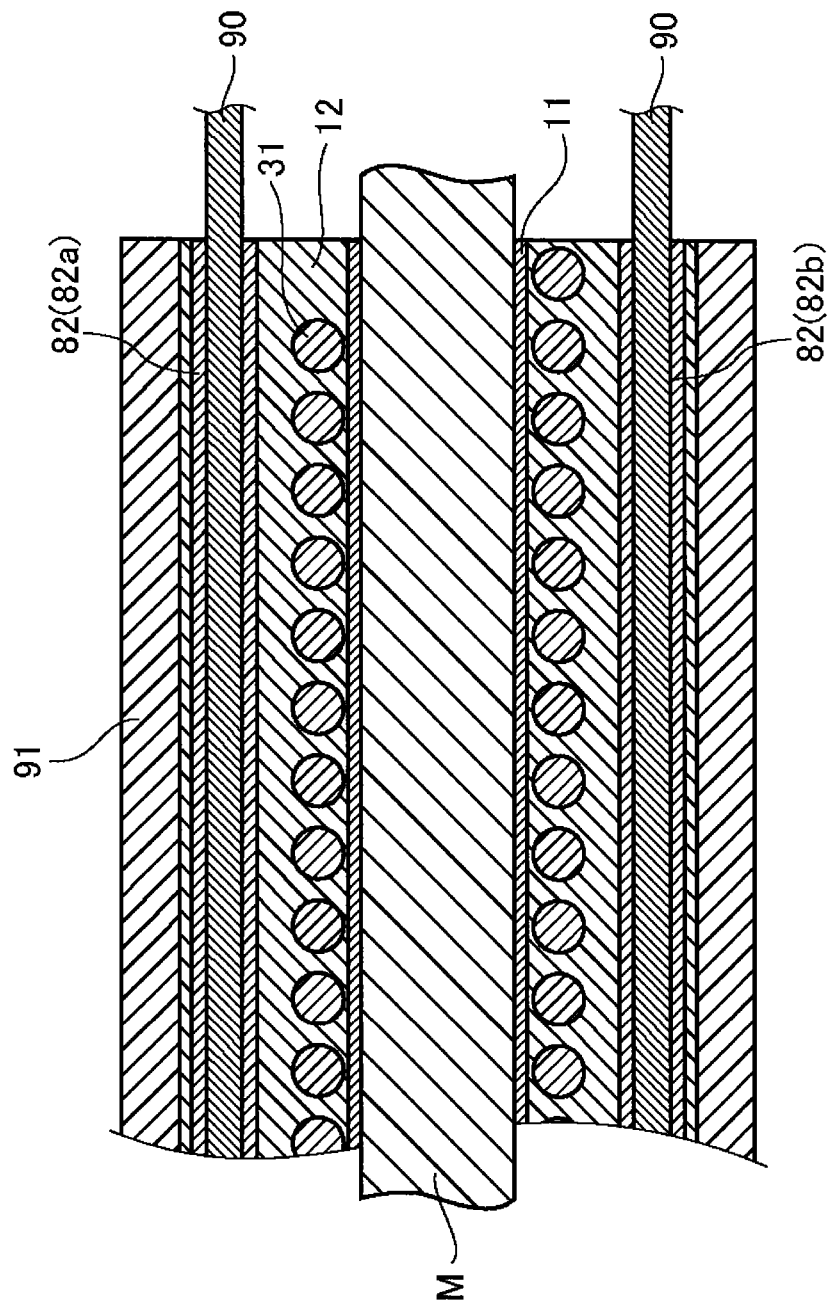
FIG. 8 is a cross-sectional view showing the manufacturing process of the catheter.

Thereafter, as shown in FIG. 8, a heat-shrinkable tube 91 is put on the periphery of the outer layer 12. The coil 31 is omitted in FIG. 8. At this time, the sublumen within the hollow tube 82 is circular in a cross-section orthogonal to the longitudinal direction thereof.

Next, the heat-shrinkable tube 91 is shrunk by heating to pressurize the outer layer 12, the coil 31, the inner layer 11, and the hollow tube 82 from the outside toward a radial direction of the inner layer 11. Additionally, the outer layer 12 is melted by the heating. In addition, the heating temperature is higher than the melting temperature of the outer layer 12 and is lower than the melting temperature of the inner layer 11 and the hollow tube 82. Through this heating, the outer layer 12 and the inner layer 11 are joined together by welding. At this time, a material that constitutes the outer layer 12 encapsulates the coil 31, and the coil is impregnated in the outer layer 12. Additionally, the outer layer 12 and the hollow tube 82 are joined together by welding.

In addition, in this process, an outer peripheral surface of the outer layer 12 is tightened by the heat-shrinkable tube 91 whereby the outer peripheral surface of the outer layer 12 becomes nearly circular.

Meanwhile, although the hollow tube 82 is pressurized in this process, since the core wire 90 brought into close contact with the inner surface of the hollow tube 82 is inserted into the hollow tube 82, the hollow tube 82 is prevented from being crushed.

Here, when the outer layer 12, the coil 31, the inner layer 11, and the hollow tube 82 are pressurized by the heat-shrinkable tube 91, it is preferable to fix both end portions of the core wire 90 to apply a tension (a first tension) to the core wire 90. At this time, the tension applied to the core wire 90 is set to a force such that the core wire 90 does not elongate. In addition, a tension may be or may not be applied to the mandrel M.

Figure 9:
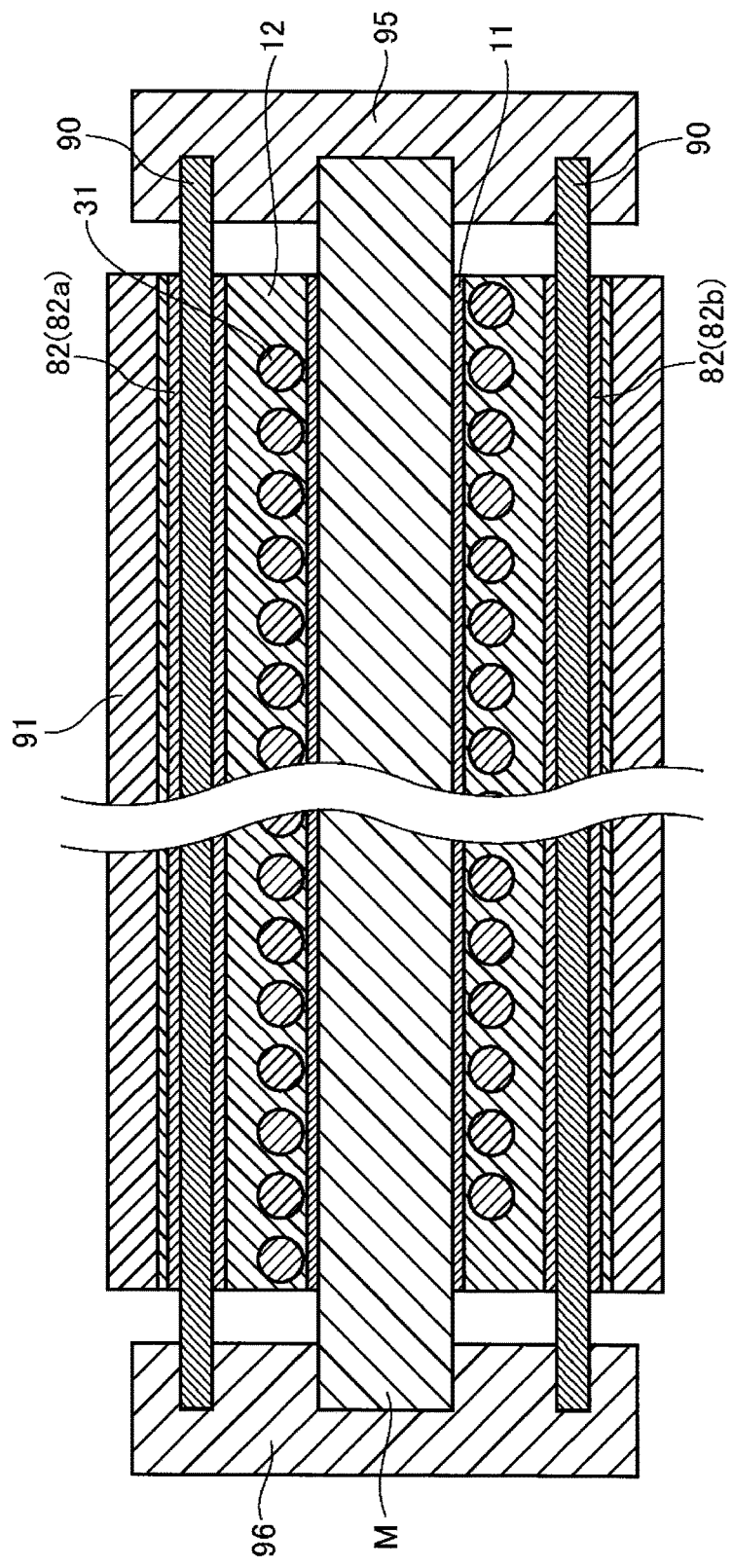
FIG. 9 is a cross-sectional view showing the manufacturing process of the catheter.

For example, as shown in FIG. 9, a pair of jigs 95 and 96 is prepared. The core wire 90 is fixed to the mandrel M in a state where the first tension is applied to the core wire 90. This allows the position of the core wire 90 with respect to the mandrel M to be fixed. Specifically, one end portion of the core wire 90 and one end portion (an end portion on the same side as one end portion of the core wire 90) of the mandrel M are fixed to the jig 95. Additionally, the other end portion of the core wire 90 and the other end portion of the mandrel M are fixed to the jig 96.

Next, the heat-shrinkable tube 91 is removed from the outer layer 12 by making a cut in the heat-shrinkable tube 91 and tearing the heat-shrinkable tube 91.

Thereafter, the core wire 90 is extracted from the inside of the hollow tube 82. At this time, the mandrel M may be simultaneously extracted.

By pulling the pair of jigs 95 and 96 so as to be spaced apart from each other, a greater tension than the above-described first tension is applied to the core wire 90 and the mandrel M, and the core wire 90 and the mandrel M are elongated and reduced in diameter. Accordingly, the core wire 90 is peeled off from the inner surface of the hollow tube 82. Additionally, the mandrel M is peeled off from the inner layer 11. Thereafter, the core wire 90 is taken out from the inside of the hollow tube 82, and the mandrel M is extracted from the inside of the inner layer 11. The core wire 90 and the mandrel M may be simultaneously extracted or may be separately extracted. A hollow portion serving as the main lumen 20 is formed at the center of the inner layer 11.

Next, an operating wire 70 is inserted through the sublumen within the hollow tube 82. The operating wire 70 is loosely inserted to the sublumen of the hollow tube 82.

Additionally, a marker 40 that is an annular metal member is separately prepared.

Next, the fixation of a tip portion of the operating wire 70 to the marker 40 and the caulking fixation of the marker 40 to the periphery of a tip portion of the outer layer 12 are performed.

Next, a member (not shown) serving as an introduction port for a medical fluid or the like, is connected to a base end portion of the main lumen 20.

Next, a base end portion of the operating wire 70 is connected to the operating part that is separately made.

Next, a coating layer 50 is formed.

From the above, a catheter 100 can be obtained.

Next, the effects of the present embodiment will be described.

In the present embodiment, the hollow tube 82 is formed by melting and extruding a resin material to supply to the periphery of the core wire 90 and bringing the resin material into direct contact with the core wire 90. The inner surface of the hollow tube 82 and the core wire 90 are brought into a close contact state. Since the core wire is inserted into the hollow tube 82 in a close contact state and the hollow tube 82 is reinforced from the inside, the shape of the hollow tube 82 is prevented from being deformed in the manufacturing process of the catheter 100.

Particularly, in the present embodiment, after the hollow tube 82 is inserted into the hollow portion of the outer layer 12, the heat-shrinkable tube 91 is shrunk, and the outer layer 12, the hollow tube 82, and the like are pressurized toward the radial direction of the outer layer 12 from the outside. Since the core wire 90 is inserted into the hollow tube 82 in a close contact state and the hollow tube 82 is reinforced from the inside, the shape of the hollow tube 82 can be prevented from being deformed in this pressurizing process.

Accordingly, the hollow tube 82 in which the sublumen 80 with a desired shape is formed can be obtained.

Additionally, the core wire 90 can be easily removed from the hollow tube 82, since the core wire 90 may be elongated and reduced in diameter so as to peel off the hollow tube 82 and the core wire 90 when the core wire 90 is removed from the hollow tube 82.

Additionally, in the present embodiment, the outer layer 12, the coil 31, the inner layer 11, and the hollow tube 82 are pressurized by the heat-shrinkable tube 91 in a state where a tension is applied to the core wire 90. It is difficult to thermally shrink the heat-shrinkable tube 91 uniformly along the longitudinal direction of the heat-shrinkable tube 91, and a portion with a strong shrinkage force and a portion with a weak shrinkage force are locally formed. Since variation occurs in the pressurizing using the heat-shrinkable tube 91, the hollow tube 82 may approach the main lumen 20 in a region where a pressure applied to the hollow tube 82 is high, and the hollow tube 82 may be spaced apart from the main lumen 20 in a region where the pressure applied to the hollow tube 82 is low.

However, in the present embodiment, the end portion of the core wire 90 brought into close contact with the inner surface of the hollow tube 82 is fixed, and a tension is applied to the core wire 90. Accordingly, the positional deviation of the core wire 90 with respect to the main lumen 20 does not occur easily even if variation occurs in the pressurizing of the hollow tube 82 by the heat-shrinkable tube 91. Therefore, the positional deviation of the hollow tube 82 covering the core wire 90 with respect to the main lumen 20 can be suppressed.

Moreover, in the present embodiment, the respective end portions of the core wire 90 are fixed to the mandrel M through the respective jigs 95 and 96. Therefore, the mandrel M inside the inner layer 11, and the core wire 90 can be simultaneously elongated and reduced in diameter by pulling the pair of jigs 95 and 96 so as to be spaced apart from each other. This can reduce the number of steps of the manufacturing process.

Additionally, in the present embodiment, the hollow tube 82 is formed by melting and extruding a resin material to supply to the periphery of the core wire 90 and bringing the resin material into direct contact with the core wire 90. Therefore, the protrusions 901 and the recesses 902 formed on the outer peripheral surface of the core wire 90 can be transferred to the inner surface of the hollow tube 82, and the hollow tube 82 having the recesses 821 and the protrusions 822 formed on the inner surface thereof can be easily manufactured.

By appropriately selecting the diameter and shape of the operating wire 70 with respect to the recesses 821 and the protrusions 822, the area of contact between the inner surface of the hollow tube 82 and the operating wire 70 can be reduced, and it is possible to enhance the operativity of the operating wire 70.

Additionally, the plurality of recesses 821 are arranged apart from each other along the longitudinal direction of the hollow tube 82. When the operating wire 70 is pulled and operated, a region between the recesses 821 in the inner surface of the hollow tube 82, and the operating wire 70 come into contact with each other, and the operating wire 70 does not easily come into contact with bottom portions of the recesses 821. This can reduce the area of contact between the inner surface of the hollow tube 82 and the operating wire 70.

Moreover, the plurality of recesses 821 are arranged apart from each other along the longitudinal direction of the hollow tube 82. Accordingly, for example, even if there is any significantly broad recess 821 among the plurality of recesses 821, the total length of the operating wire 70 can be prevented from getting stuck into one recess. Therefore, the operativity of the operating wire 70 can be prevented from being hindered.

Similarly, since the plurality of protrusions 822 are arranged apart from each other along the longitudinal direction of the hollow tube 82, the area of contact between the operating wire 70 and the inner surface of the hollow tube 82 can be reduced by the operating wire 70 coming into contact with the protrusions 822 adjacent to each other in the longitudinal direction so as to straddle between the protrusions.

In addition, the invention is not limited to the aforementioned embodiment, and alternations, improvements, or the like within the scope that the object of the invention can be achieved will be included in the invention.

For example, in the aforementioned embodiment, the hollow tube 82 is inserted into the hollow portion of the outer layer 12 after the outer layer 12 is formed. However, the invention is not limited to such a manufacturing method. For example, the hollow tube 82 having the core wire 90 inserted thereinto may be arranged on the outer peripheral side of the main lumen forming region of the outer layer 12 by melting and extruding the resin material constituting the outer layer 12 after the hollow tube 82 with the core wire 90 is arranged around the inner layer 11.

Moreover, in the aforementioned embodiment, the mandrel M and the core wire 90 are simultaneously elongated and reduced in diameter. However, the invention is not limited to this. For example, the mandrel M may be elongated and reduced in diameter and may be extracted from the inner layer 11 after the core wire 90 is elongated and reduced in diameter and extracted from the hollow tube 82.

Additionally, in the aforementioned embodiment, the recesses 821 and the protrusions 822 are formed on the inner surface of the hollow tube 82. However, only the recesses 821 or only the protrusions 822 may be formed.

Figure 10:
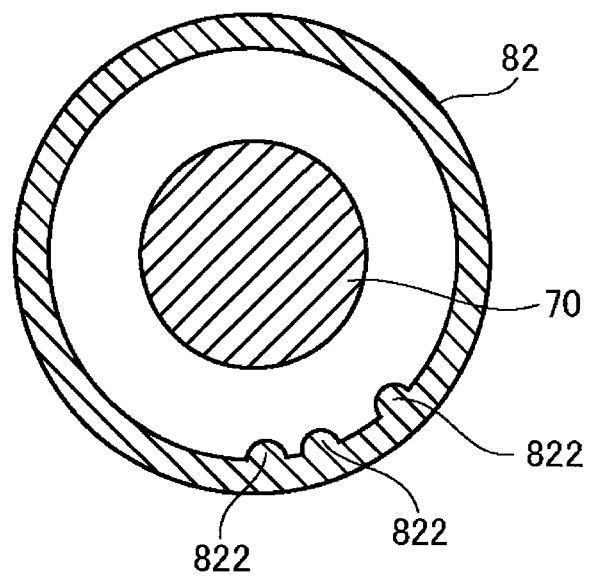
FIGS. 10(a) and 10(b) are cross-sectional views orthogonal to a longitudinal direction of a hollow tube, showing the operating wire and the hollow tube.
Figure 10:
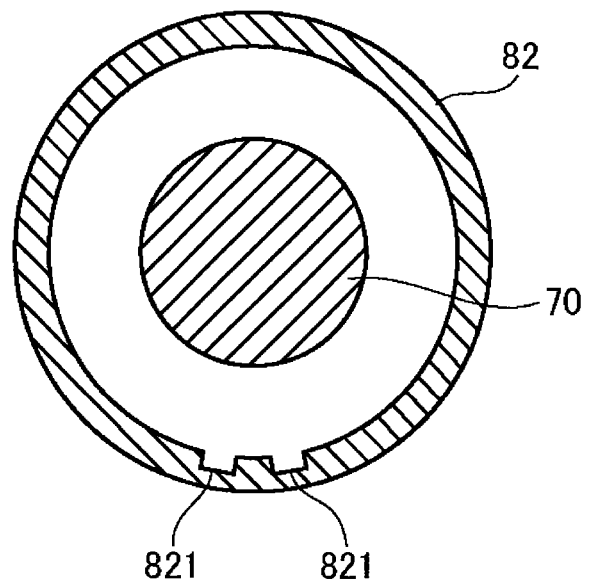

Additionally, although an example in which the operating wire 70 is a stranded wire has been shown in the aforementioned embodiment, the operating wire 70 may be a round wire as shown in FIGS. 10(a) and 10(b).

Figure 11:
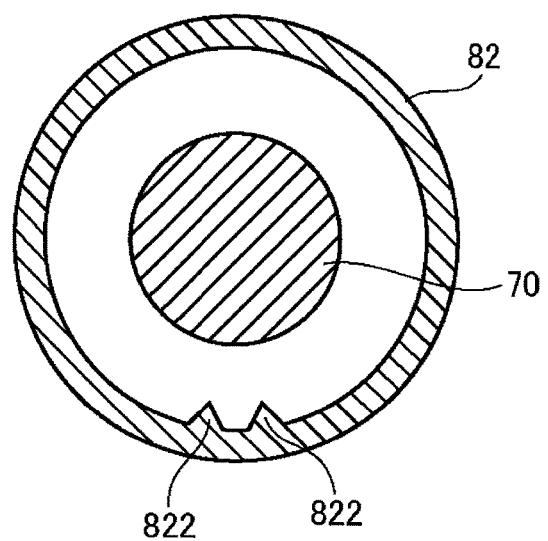
FIG. 11 is a cross-sectional view orthogonal to the longitudinal direction of the hollow tube, showing the operating wire and the hollow tube.

Moreover, although an example in which the tip surfaces of the protrusions 822 have a curved shape has been shown in the aforementioned embodiment, for example, as shown in FIG. 11, the cross-section of the protrusion 822 orthogonal to the longitudinal direction of the hollow tube may be a triangular shape, and the tip portion of the protrusions 822 may have an acute angle.

This application claims priority based on Japanese Patent Application No. 2012-41960, filed on Feb. 28, 2012, the disclosure of which is all incorporated herein by reference.

The invention claimed is:

1. A medical instrument, comprising:
a tubular body having an outer layer and a main lumen;
a hollow tube comprising a material different from the outer layer of the tubular body and embedded in the outer layer of the tubular body such that the hollow tube has an outer surface directly joined to the outer layer of the tubular body and is positioned on an outer peripheral side of the main lumen and demarcating a sublumen; and
an operating wire inserted in the sub lumen of the hollow tube such that the operating wire bends a distal end portion of the tubular body when operated at a proximal end portion of the operating wire,
wherein the hollow tube has an inner surface continuously extending in a longitudinal direction of the hollow tube and one of a plurality of recesses and a combination of a plurality of protrusions and the plurality of recesses formed on the inner surface such that at least one of the plurality of protrusions and the plurality of recesses is extending on at least one side of the inner surface in the longitudinal direction of the hollow tube and formed apart from each other along the longitudinal direction of the hollow tube and that each of the plurality of protrusions and/or the plurality of recesses does not extend over a total length of the hollow tube, and the hollow tube is formed with the plurality of recesses such that each of the plurality of recesses has a width having a length orthogonal to a depth direction and a longitudinal direction of the plurality of recesses and that the width of each of the plurality of recesses is set smaller than a diameter of the operating wire.

2. The medical instrument according to claim 1, wherein the hollow tube is formed with the plurality of protrusions such that each of the plurality of protrusions has a curvature radius which is smaller than a curvature radius of the operating wire.

3. The medical instrument according to claim 2, wherein the hollow tube is formed such that each of the plurality of recesses has a length in the longitudinal direction which is greater than the width.

4. The medical instrument according to claim 2, wherein the hollow tube is formed such that the plurality of recesses includes recesses which are different from each other in at least one of a length in the longitudinal direction, a depth, the width and a cross-sectional shape.

5. The medical instrument according to claim 1, wherein the operating wire is a stranded wire comprising a plurality of thin twisted wires, and each of the plurality of protrusions has a height and a width which are smaller than a diameter of an inscribed circle coming into contact with a circumscribed circle of the stranded wire and two adjacent thin twisted wires forming an outer peripheral portion of the stranded wire.

6. The medical instrument according to claim 5, wherein the hollow tube is formed with the plurality of protrusions such that each of the plurality of protrusions has a curvature radius which is smaller than a curvature radius of the operating wire.

7. The medical instrument according to claim 5, wherein the hollow tube is formed such that each of the plurality of recesses has a length in the longitudinal direction which is greater than the width.

8. The medical instrument according to claim 1, wherein the hollow tube has the combination of the plurality of protrusions and the plurality of recesses formed on the inner surface such that the plurality of protrusions and the plurality of recesses are extending in the longitudinal direction of the hollow tube and formed apart from each other along the longitudinal direction of the hollow tube.

9. The medical instrument according to claim 1, wherein the material of the hollow tube has bending rigidity and tensile elasticity which are higher than the outer layer of the tubular body.

10. The medical instrument according to claim 9, wherein the hollow tube is formed such that each of the plurality of recesses has a length in the longitudinal direction which is greater than the width.

11. The medical instrument according to claim 9, wherein the hollow tube is formed such that the plurality of recesses includes recesses which are different from each other in at least one of a length in the longitudinal direction, a depth, the width and a cross-sectional shape.

12. The medical instrument according to claim 9, wherein at least one of the plurality of protrusions and the plurality of recesses is aligned in the longitudinal direction of the hollow tube and formed apart from each other along the longitudinal direction of the hollow tube.

13. The medical instrument according to claim 1, wherein the hollow tube is formed such that each of the plurality of recesses has a length in the longitudinal direction which is greater than the width.

14. The medical instrument according to claim 1, wherein the hollow tube is formed such that the plurality of recesses includes recesses which are different from each other in at least one of a length in the longitudinal direction, a depth, the width and a cross-sectional shape.

15. The medical instrument according to claim 1, wherein at least one of the plurality of protrusions and the plurality of recesses is aligned in the longitudinal direction of the hollow tube and formed apart from each other along the longitudinal direction of the hollow tube.

16. The medical instrument according to claim 15, wherein the hollow tube is formed with the plurality of protrusions such that each of the plurality of protrusions has a curvature radius which is smaller than a curvature radius of the operating wire.

17. The medical instrument according to claim 15, wherein the hollow tube is formed such that the plurality of recesses includes recesses which are different from each other in at least one of a length in the longitudinal direction, a depth, the width and a cross-sectional shape.

18. The medical instrument according to claim 15, wherein the hollow tube is formed such that the plurality of protrusions includes protrusions which are different from each other in at least one of a length in the longitudinal direction, a height, a width and a cross-sectional shape.

19. The medical instrument according to claim 1, wherein the hollow tube is formed such that the hollow tube has a roughened outer peripheral surface.

20. The medical instrument according to claim 1, wherein the hollow tube is formed such that the plurality of protrusions includes protrusions which are different from each other in at least one of a length in the longitudinal direction, a height, a width and a cross-sectional shape.

* * * * *